United States Patent
Kinicki et al.

(10) Patent No.: US 6,464,636 B1
(45) Date of Patent: Oct. 15, 2002

(54) CONFIGURATION TOOL FOR USE IN ULTRASOUND IMAGING DEVICE

(75) Inventors: Rachel M. Kinicki, Acton, MA (US); Daniel Gerard Maier, Methuen, MA (US); Charles R. Dowdell, Nashua, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 13 days.

(21) Appl. No.: 09/691,599

(22) Filed: Oct. 18, 2000

(51) Int. Cl.[7] .................................................. A61B 8/00
(52) U.S. Cl. ............................................................ 600/437
(58) Field of Search ................................. 600/443, 447, 600/437, 459, 444, 438

(56) References Cited

U.S. PATENT DOCUMENTS

| | | | |
|---|---|---|---|
| 5,549,111 A | 8/1996 | Wright et al. | 128/742 |
| 5,560,362 A | 10/1996 | Sliwa, Jr. et al. | 128/660.03 |
| 5,623,928 A | 4/1997 | Wright et al. | 128/661.01 |
| 5,676,147 A | 10/1997 | Petrofsky et al. | 128/661.01 |
| 5,715,823 A | 2/1998 | Wood et al. | 128/660.01 |
| 5,722,412 A | 3/1998 | Pflugrath et al. | 128/662.03 |
| 5,740,128 A | 4/1998 | Hossack et al. | 367/138 |
| 5,851,186 A | 12/1998 | Wood et al. | 600/437 |
| 5,879,303 A | 3/1999 | Averkiou et al. | 600/447 |
| 5,891,035 A * | 4/1999 | Wood et al. | 600/437 |
| 5,924,988 A | 7/1999 | Burris et al. | 600/437 |
| 5,997,478 A * | 12/1999 | Jackson et al. | 600/437 |
| 6,063,030 A * | 5/2000 | Vara et al. | 600/437 |
| 6,159,150 A * | 12/2000 | Yale et al. | 600/437 |
| 6,272,469 B1 * | 8/2001 | Koritzinsky et al. | 702/2 |

* cited by examiner

Primary Examiner—Francis J. Jaworski
Assistant Examiner—Maulin Patel
(74) Attorney, Agent, or Firm—John Vodopia (57) ABSTRACT

A software program executing externally to an ultrasound imaging device. The software program enters user control values for the ultrasound imaging device and calculates parameters based on the entered user control values. The parameters are then transferred to and stored in the ultrasound imaging device. The ultrasound imaging device includes parametrically defined machines controlled by the stored parameters to generate ultrasound images.

21 Claims, 8 Drawing Sheets

| Color Scanning Windows | | | | | |
|---|---|---|---|---|---|

Please enter the desired number of horizontal and vertical color wedge positions. Enter the radial upper and lower boundaries [0-100%] and the first and last line positions [-90deg - +90deg] in units of 128th degrees.

Go    OK    Cancel

Enter wedge positions in order from top to bottom of image and from left to right in image.

2.5 MHz sector

Maximum number of wedge positions [num horizontal * num vertical]: 35

Number of Horizontal positions: 7

Number of Vertical positions: 5

Enter the color scanning window horizontal default location: 3

Enter the color scanning window vertical default location: 2

| Wedge | Inner Radius | Outer Radius | First Line | Last Line |
|---|---|---|---|---|
| 0 | 3 | 45 | -5568 | -2112 |
| 1 | 13 | 58 | -5568 | -2112 |
| 2 | 27 | 72 | -5568 | -2112 |
| 3 | 41 | 86 | -5568 | -2112 |
| 4 | 55 | 99 | -5568 | -2112 |
| 5 | 3 | 45 | -4416 | -960 |
| 6 | 13 | 58 | -4416 | -960 |
| 7 | 27 | 72 | -4416 | -960 |
| 8 | 41 | 86 | -4416 | -960 |
| 9 | 55 | 99 | -4416 | -960 |
| 10 | 3 | 45 | -3072 | 384 |
| 11 | 13 | 58 | -3072 | 384 |

CONFIGURATION TOOL FOR USE IN ULTRASOUND IMAGING DEVICE

BACKGROUND OF THE INVENTION

1. Field of the Invention

The present invention relates to ultrasound imaging devices. More particularly, the present invention relates a software program, executing externally to an ultrasound imaging device, for configuring the ultrasound imaging device.

2. Description of the Related Art

Ultrasound imaging devices are used to generate an ultrasound image of the inside of a person's body. Such ultrasound imaging devices typically include a large number of user controls located on the ultrasound imaging device to allow an end user (such as a doctor, nurse or technician) to set the conditions for generating the ultrasound image. For example, such user controls might allow the end user to set the depth at which the ultrasound image will be taken, color scales for the ultrasound image, etc.

After the user controls are set, the ultrasound image device computes parameters in real-time for taking the ultrasound image. The parameters are computed in accordance with the conditions set with the user controls. The ultrasound imaging devices then uses these computed parameters to generate the ultrasound image.

Unfortunately, conventional ultrasound imaging devices require a large number of user controls to allow for the many possible combination of settings. Such use of a large number of user controls on the ultrasound imaging device is confusing to the end user, and difficult for the end user to learn.

Moreover, the real-time computation of parameters has some serious disadvantages. For example, the software required to provide real-time computation is relatively complex to design. In addition, real-time computation causes an annoying delay between the time the user controls are set and the time the ultrasound image can be generated, due to the time required to perform the computation.

SUMMARY OF THE INVENTION

The present is directed to providing a software program executing externally to an ultrasound imaging device. The software program enters user control values for the ultrasound imaging device and calculates parameters based on the entered user control values. The parameters are transferred to the ultrasound imaging device and control parametrically defined machines in the ultrasound imaging device to generate ultrasound images.

The present invention is also directed to providing an apparatus which includes an ultrasound imaging device and a software program executing externally to the ultrasound imaging device. The software program enters user control values for the ultrasound imaging device and calculates parameters based on the entered user control values. The parameters are transferred to the ultrasound imaging device. The ultrasound imaging device includes at least one parametrically defined machine controlled by the transferred parameters to generate ultrasound images.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Reference will now be made in detail to the present preferred embodiments of the present invention, examples of which are illustrated in the accompanying drawings, wherein like reference numerals refer to like elements throughout.

Figure 1:
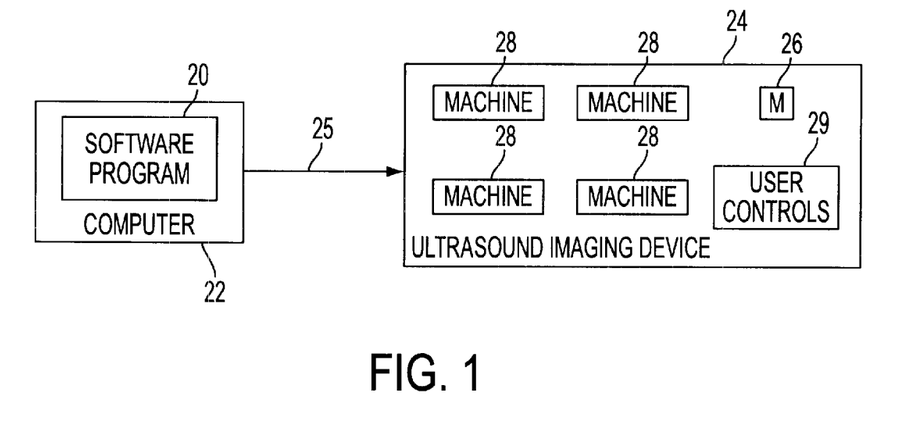
FIG. 1 is a diagram illustrating the use of a software program external to an ultrasound imaging device, according to an embodiment of the present invention.
Figure 2:
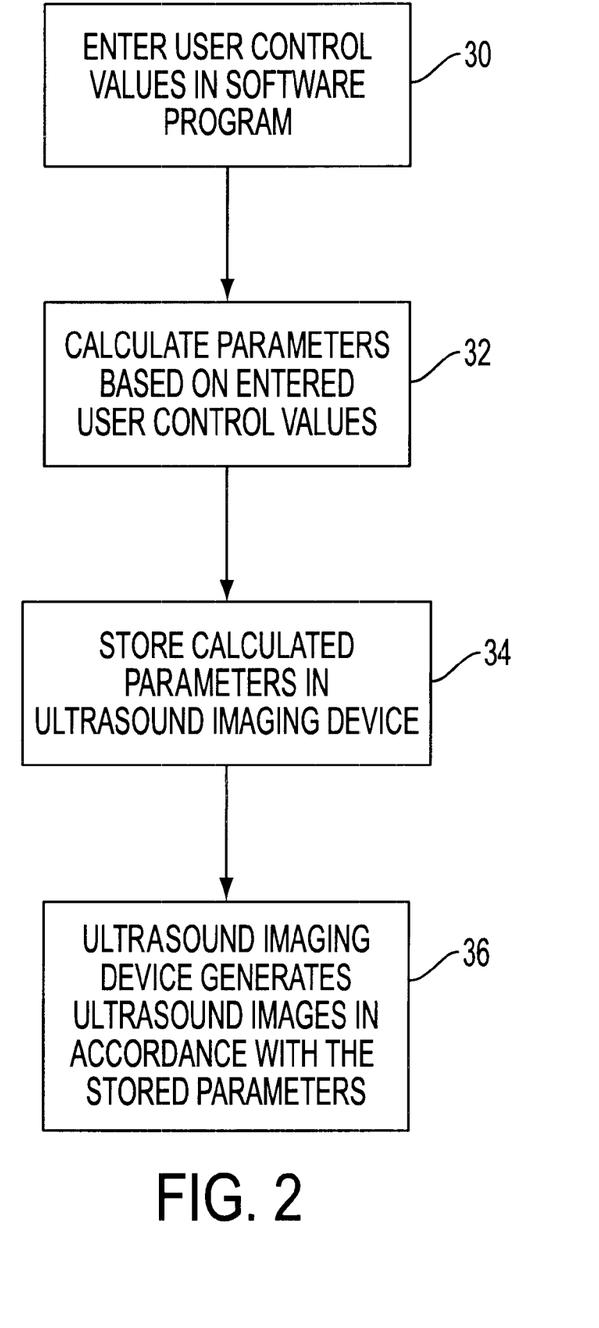
FIG. 2 is a diagram illustrating the operation of a software program, according to an embodiment of the present invention.

FIG. 1 is a diagram illustrating the use of a software program external to an ultrasound imaging device, according to an embodiment of the present invention. Referring now to FIG. 2, a software program 20 executes on a computer 22. Software program 20 is external to an ultrasound imaging device 24. Similarly, computer 22 is external to ultrasound imaging device 24. Here, being "external" indicates that software program 20 and computer 22 are not housed in the same enclosure as ultrasound imaging device 24, and can operate independent of the operation of ultrasound imaging device 24. For example, software program 20 might be executable on computer 22 located in an engineering facility or factory far from a doctor's office where ultrasound imaging device 24 might be located.

Software program 20 provides a virtual control panel (not illustrated in FIG. 1) with a plurality of user controls which can be set to enter user control values into software program 20. The user control values would typically be entered into software program 20 by an ultrasound technician or engineer, not by an end user of ultrasound imaging device 24. However, the present invention is not limited in this manner. For example, in some situations, an end user of ultrasound imaging device 24 might enter user control values into software program 20.

After user control values are entered in software program 20, software program 20 calculates parameters based on the entered user control values.

As indicated by communication line 25, the calculated parameters are then loaded from computer 22 into ultrasound imaging device 24, and stored in memory (M) 26. Memory 26 might be, for example, ROM or RAM, but the present invention is not limited to memory 26 being any particular type of memory.

In a typical scenario, the parameters would be calculated by software program 20 at a factory or engineering facility, and then later loaded into ultrasound imaging device 24 while ultrasound imaging device 24 is also at the factory or engineering facility, before being shipped to end users. In another example of a typical scenario, ultrasound imaging device 24 might be located at the site of an end user, such as at a doctor's office or hospital. The parameters can be calculated offline by software program 20 at a remote location, and then later loaded into ultrasound imaging device 24 at the site of the end user. Of course, the present invention is not limited to software program 20 and/or ultrasound imaging device 24 being in any particular location when the parameters are calculated and/or loaded into ultrasound imaging device 24.

By calculating parameters offline and then later loading the parameters into ultrasound imaging device 24, end users of ultrasound imaging device 24 do not need to be aware of the various activities performed by engineers or technicians to enter user control values and calculate parameters. For example, if the user control values are entered and the parameters are calculated at a factory, end users of ultrasound imaging device 24 do not need to be aware of the activities performed at the factory.

Although communication line 25 indicates a direct transfer, the present invention is not limited to such a direct transfer. For example, there may be some intermediary between computer 22 and ultrasound imaging device 24 to transfer the calculated parameters from computer 22 to ultrasound imaging device 24. Moreover, a flash card, floppy disk, optical disk, or some other type of moveable memory can be used to load parameters into ultrasound imaging device 24. Further, there are many ways for computer 22 to communicate with ultrasound imaging device 24, and the present invention is not limited to any particular way. For example, communication line 25 could be a cable or wireless communication channel connecting computer 22 and ultrasound imaging device 24. As an additional example, communication line 25 might be the Internet.

Ultrasound imaging device 24 includes a plurality of machines 28. Machines 28 are parametrically defined machines which are controlled by the parameters stored in memory 26 to generate ultrasound images. Here, the term "parametrically defined" machine indicates a machine that performs an operation based on a parameter provided to the machine. The concept of a parametrically defined machine would be well understood in the art. In fact, conventional ultrasound imaging devices include parametrically defined machines since such machines are controlled in accordance with parameters. However, a conventional ultrasound imaging device would calculate the parameters in real-time, and then immediately use those real-time calculated parameters. Thus, the present invention calculates the parameters externally to the ultrasound imaging device and then loads the calculated parameters into ultrasound imaging device 24, whereas a conventional ultrasound imaging device calculates the parameters in real time inside the ultrasound imaging device.

Machines 28 can be many types of typical machines used to generate ultrasonic images, such as those required to transmit ultrasound energy and receive a signal generated in tissue by the transmitted ultrasound energy. For example, machines 28 might include a detector, a time gain compensator and a scan converter. However, the present invention is not limited to these examples, or to any specific types of machines 28. Here, the term "machine" simply indicates a device which automatically performs an operation in accordance with the purpose of the device. Such a machine is not limited to having fixed or moving parts. Thus, a machine could be simply an integrated circuit, or chip, inside ultrasound imaging device 24. Machines 28 would be well understood in the art.

Further, FIG. 1 shows ultrasound imaging device 24 as having four separate machines 28. However, the present invention is not limited to any particular number of machines 28. Instead, ultrasound imaging device 24 should simply have one or more machines 28.

Ultrasound imaging device 24 has user controls 29 thereon, to allow an end user to set user control values. User controls 29 are physical knobs or buttons which are accessible to end users. Alternatively, user controls 29 could be virtual user controls provided on a screen display by ultrasound imaging device 24.

Ultrasound imaging device 24 could be a stationary or portable ultrasound imaging device. For example, ultrasound imaging device 24 could be a portable ultrasonic imaging device, and might weigh less than 15 lbs. However, ultrasound imaging device 24 is not limited to being any particular size.

Computer 22 is not limited to being any particular type of computer, and might be, for example, a mainframe computer, a minicomputer, a desktop computer, a laptop computer, a personal digital assistant (PDA), or any other type of portable computing device or other computing device capable of executing software program 20. In a typical scenario, computer 22 might be a laptop computer running a standard MICROSOFT WINDOWS based operating system. With such a configuration, software program 20 can be a relatively simple program running in an inexpensive environment for calculating parameters. Of course, the present invention is not limited to any particular operating system running on computer 22.

Therefore, with software program 20 and ultrasound imaging device 24 in FIG. 1, a non-end user (such as, for example, an engineer, ultrasound technician, etc.) can enter user control values into software program 20. Software program 20 then calculates parameters in accordance with the entered user control values. In a typical scenario, software program 20 calculates the parameters offline with respect to the operation of ultrasound imaging device 24.

The calculated parameters are then loaded into ultrasound imaging device 24 and stored in memory 26. Thereafter, machines 28 in ultrasound imaging device 24 are controlled in real-time by the stored parameters to generate ultrasound images. In this manner, the parameters can be calculated offline, not in real-time, by software program 20. With such offline calculation, calculation time is not as important, and the software required to perform the calculations is not as complex, as compared to real-time calculation.

In a typical configuration, all parametric calculations are performed by software program 20, as opposed to ultrasound imaging device 24. Thus, in such a typical configuration, ultrasound imaging device 24 would not perform calculations to arrive at the parameters. Instead, to generate an ultrasound image, ultrasound imaging device 24 simply accesses the pre-calculated parameters. In this manner, the real-time generation of ultrasound images by ultrasound imaging device 24 will be relatively quick, since the parameters are not calculated by ultrasound image device 24. However, the present invention may also be applicable to an ultrasound imaging device 24 which performs some types of parametric calculation therein.

There is a very large universe of possible combinations of user control values that can be used to control ultrasound imaging device 24. The user control values entered into software program 20 are a subset of this large universe of possible combinations. Therefore, according to embodiments of the present invention, instead of having a large number of possible combinations of user control values selectable by an end user of ultrasound imaging device 24 via user controls 29, the present invention allows a smaller subset of the possible combinations to be loaded into ultrasonic imaging device 24. Since the end user of ultrasound imaging device 24 can only select from the combinations of user control values actually loaded into ultrasound imaging device 24, ultrasound imaging device 24 would only have to provide sufficient user controls 29 for selecting the loaded combinations of user control values. Therefore, by reducing the number of user controls 29 and possible combinations of user control values selectable by end users of ultrasonic imaging device 24, the present invention provides an easier-to-use ultrasonic imaging device 24 from the perspective of the end user. This is a significant advantage, as a typical end user (such as a doctor), typically prefers a simple, easy-to-use, device. Such easy-of-use is very important when the end user is not specifically trained in using ultrasonic imaging devices.

The various user controls 29 provided to an end user by ultrasound imaging device 24 can easily be changed in accordance with the loaded user control values, by using a virtual control panel on ultrasound imaging device 24. Further, by using a virtual control panel on ultrasound imaging device 24, the various user controls and user control values made available to the end user can be high organized in a manner that would not be possible with a non-virtual control panel.

Further, according to embodiments of the present invention, a engineer or other non-end user can obtain information from many doctors, and then determine an appropriate subset of user control values of the larger universe of possible combinations of user control values. The non-end user can then enter this subset of user control values into computer program 20 to calculate appropriate parameters offline. These calculated parameters can then be loaded into many different ultrasound imaging devices 24 for use by many different end users. This is a significant advantage in that the parameters for many different ultrasound imaging devices 24 can be determined and calculated in one location and/or at one time by a non-end user, and then easily loaded into the many different ultrasound imaging devices 24.

In addition, according to embodiments of the present invention, a non-end user can set user control values via software program 20, but not allow end users of ultrasound imaging device 24 to select from these set user control values. For example, an engineer at a factory might set appropriate user control values for "focus," but not allow an end user of ultrasound imaging device 24 to select from different focus parameters. For example, a "focus" control might not be provided to an end-user as a user control 29 on ultrasound imaging device 24, with all focus parameters being set by an engineer at the factory via software program 20.

Generally, by reducing the number of possible combinations of user control values selectable by end users of ultrasonic imaging device 24, the present invention can be seen as quantizing the larger universe of possible combinations of user control values down to a smaller set of useful configurations. The quantizing is performed, for example, at a factory or engineering facility by an engineer or technician in accordance with gathered data indicating the user control settings which are the most preferred by end users. The quantized, smaller set of useful configurations is loaded into ultrasound imaging device 24. As indicated above, such quantizing and loading into ultrasound imaging device 24 can be performed offline, when ultrasound imaging device 24 is not being used to generate ultrasound images. The performance of ultrasound imaging device 24 will then be greatly improved, since the quantized, smaller set of useful configuration is loaded therein, and can be quickly accessed without requiring parameter calculations. Further, ultrasound imaging device 24 will be relatively easy for an end user to use, since the most useful configurations are essentially pre-loaded therein.

Therefore, there are several different ways that software program 20 can be used with ultrasound imaging device 24. For example, with one way to use software program 20 with ultrasound imaging device 24, software program 20 is used to enter user control values and then calculate parameters based on the entered user control values. These parameters are stored in tables and linked to run-time software. The combined software (that is, the combination of software program 20 and the run-time software) is loaded into ultrasound imaging device 24 and used to control ultrasound imaging device 24.

With another way to use software program 20 with ultrasound imaging device 24, software program 20 is used to enter user control values and then calculate parameters based on the entered user control values. The parameters are then loaded directly into a connected, powered ON ultrasound imaging device 24 and replace previously stored parameters. The newly loaded parameters control ultrasound imaging device 24, but are not preserved through an OFF/ON power cycle. This technique can be used to vary the parameters in real-time in order to optimize the parameters. This technique might be used, for example, in clinical trials where an engineer works with an end user (e.g., a doctor) to determine a user control value or set of user control values to make available on ultrasound imaging device 24 for all end users.

FIG. 2 is a diagram illustrating the operation of software program 20, according to an embodiment of the present invention. Referring now to FIG. 2, in operation 30, user control values are entered into software program 20. As indicated above, the entered user control values are a subset of the total universe of user control values which are available for controlling ultrasound imaging device 24. The user control values would typically be entered by an ultrasound technician or engineer, and would typically not be entered by an end user of ultrasound imaging device 24.

From operation 30, the process moves to operation 32, where software program 20 calculates parameters based on the entered user control values.

From operation 32, the process moves to operation 34, where the calculated parameters are stored in ultrasound imaging device 24.

From operation 34, the process moves to operation 36, where ultrasound imaging device 24 generates ultrasound images in accordance with the stored parameters.

FIGS. 3–7 are diagrams illustrating an example of the operation of software program 20, according to an embodiment of the present invention.

Figure 3:
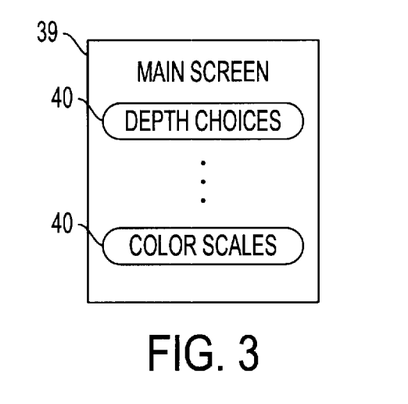
FIGS. 3–6 are diagrams illustrating an example of the operation of a software program, according to an embodiment of the present invention.

More specifically, FIG. 3 is a diagram illustrating an example of a main screen display 39 of a graphical user interface (GUI) of software program 20 executing on computer 22, according to an embodiment of the present invention. Thus, FIG. 3 represents an example of a virtual control panel provided by software program 20. Referring now to FIG. 3, a plurality of user controls 40 are shown on screen display 39. User controls 40 are, for example, virtual button or other virtual selection mechanisms. In the example of FIG. 3, the various user controls include many different user controls, including "DEPTH CHOICES" and "COLOR SCALES." Of course, the present invention is not limited to these specific user controls 40. The specific user controls and layout of screen display 39 are a matter of design choice. Moreover, the use of a GUI with virtual selection mechanisms is well known.

In this example, assume that "DEPTH CHOICES" is selected from screen display 39 by an engineer who is not an end user of ultrasound imaging device 24.

Figure 4:
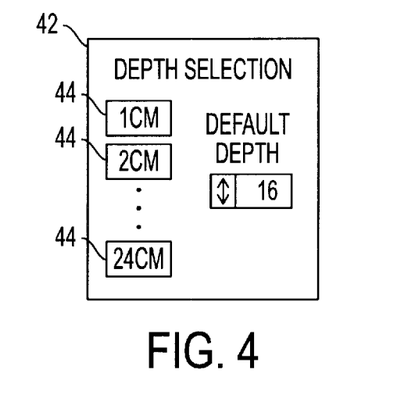

Therefore, FIG. 4 is a diagram illustrating an example of a screen display 42 which might appear after "DEPTH CHOICES" is selected in FIG. 3, according to an embodiment of the present invention. Referring now to FIG. 4, a plurality of depth selections 44 are shown, including depth selections from 1 cm to 24 cm.

In this example, assume that 8 cm, 12 cm, 16 cm, 20 cm and 24 cm, and a default depth of 16 cm, are selected from screen display 42.

Figure 5:
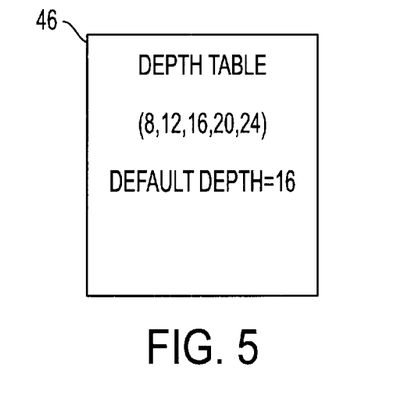

Therefore, FIG. 5 is a diagram illustrating an example of a conceptual representation of a depth table 46 which might be created by software program 20, in response to the selected depths, according to an embodiment of the present invention.

Figure 6:
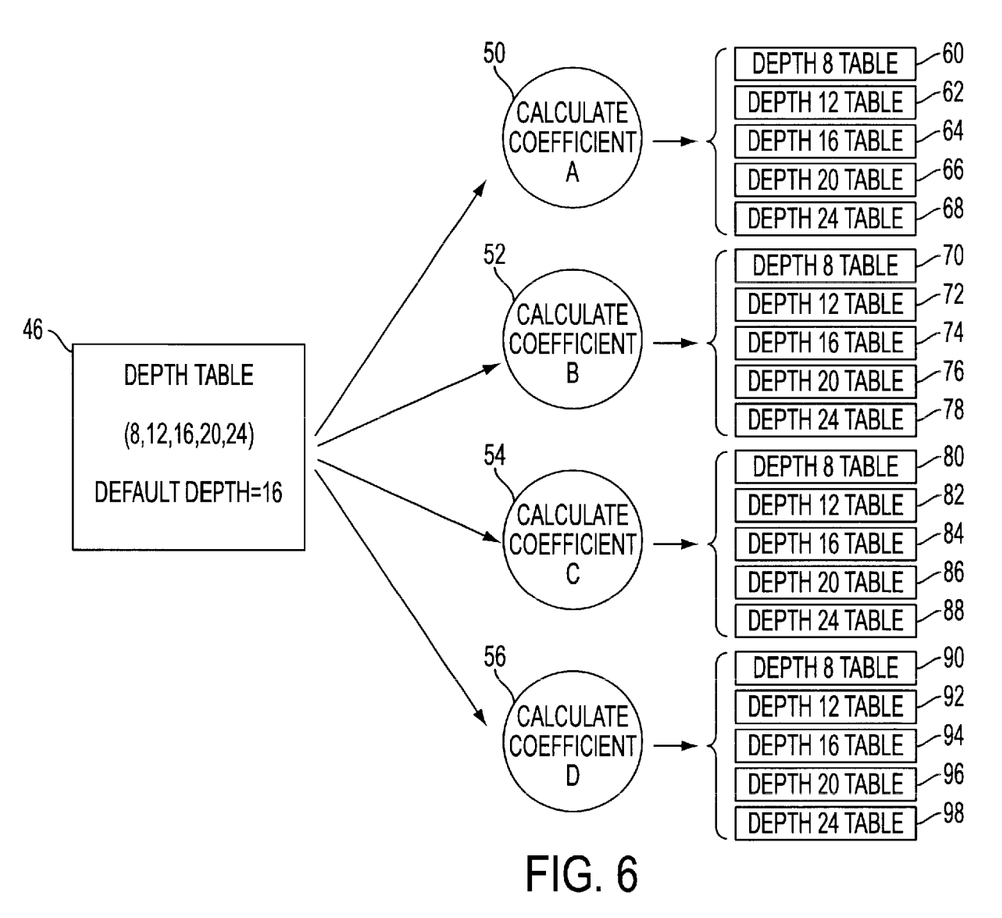

FIG. 6 is a diagram illustrating an example of the use of depth table 46, according to an embodiment of the present invention. In this example, it is assumed that machines 28 in ultrasound imaging device 24 require coefficients A, B, C and D. Of course, while four coefficients are used in this example, the present invention is not limited to any specific number of coefficients.

Referring now to FIG. 6, the calculation of coefficients A, B, C and D is indicated by reference numerals 50, 52, 54 and 56, respectively. More specifically, software program 20 calculates coefficients A, B, C and D for each of the depths of 8, 12, 16, 20 and 24 in depth table 46. The calculated coefficient A for depths 8, 12, 16, 20 and 24 are stored in tables 60, 62, 64, 66 and 68, respectively. The calculated coefficient B for depths 8, 12, 16, 20 and 24 are stored in tables 70, 72, 74, 76 and 78, respectively. The calculated coefficient C for depths 8, 12, 16, 20 and 24 are stored in tables 80, 82, 84, 86 and 88, respectively. The calculated coefficient D for depths 8, 12, 16, 20 and 24 are stored in tables 90, 92, 94, 96 and 98, respectively. Of course, the present invention is not limited to any specific correlation of tables to coefficients.

The data stored in tables 60, 62, 64, 66, 68, 70, 72, 74, 76, 78, 80, 82, 84, 86, 88, 90, 92, 94, 96 and 98 are the parameters that will be used by ultrasound machine 24 to generate ultrasound images. Thus, after the data in tables 60, 62, 64, 66, 68, 70, 72, 74, 76, 78, 80, 82, 84, 86, 88, 90, 92, 94, 96 and 98 is determined, this data is stored in memory 26.

When generating an ultrasonic image, machines 28 that require coefficient A would obtain the required coefficient from one of tables 60, 62, 64, 66 and 68 based on whether depth 8, 12, 16, 20 or 20, respectively, was selected by an end user of ultrasound imaging device 24. Machines 28 that require coefficient B would obtain the required coefficient from one of tables 70, 72, 74, 76 and 78 based on whether depth 8, 12, 16, 20 or 20, respectively, was selected by an end user of ultrasound imaging device 24. Machines 28 that require coefficient C would obtain the required coefficient from one of tables 80, 82, 84, 86 and 88 based on whether depth 8, 12, 16, 20 or 20, respectively, was selected by an end user of ultrasound imaging device 24. Machines 28 that require coefficient D would obtain the required coefficient from one of tables 90, 92, 94, 96 and 98 based on whether depth 8, 12, 16, 20 or 20, respectively, was selected by an end user of ultrasound imaging device 24.

Figure 7:
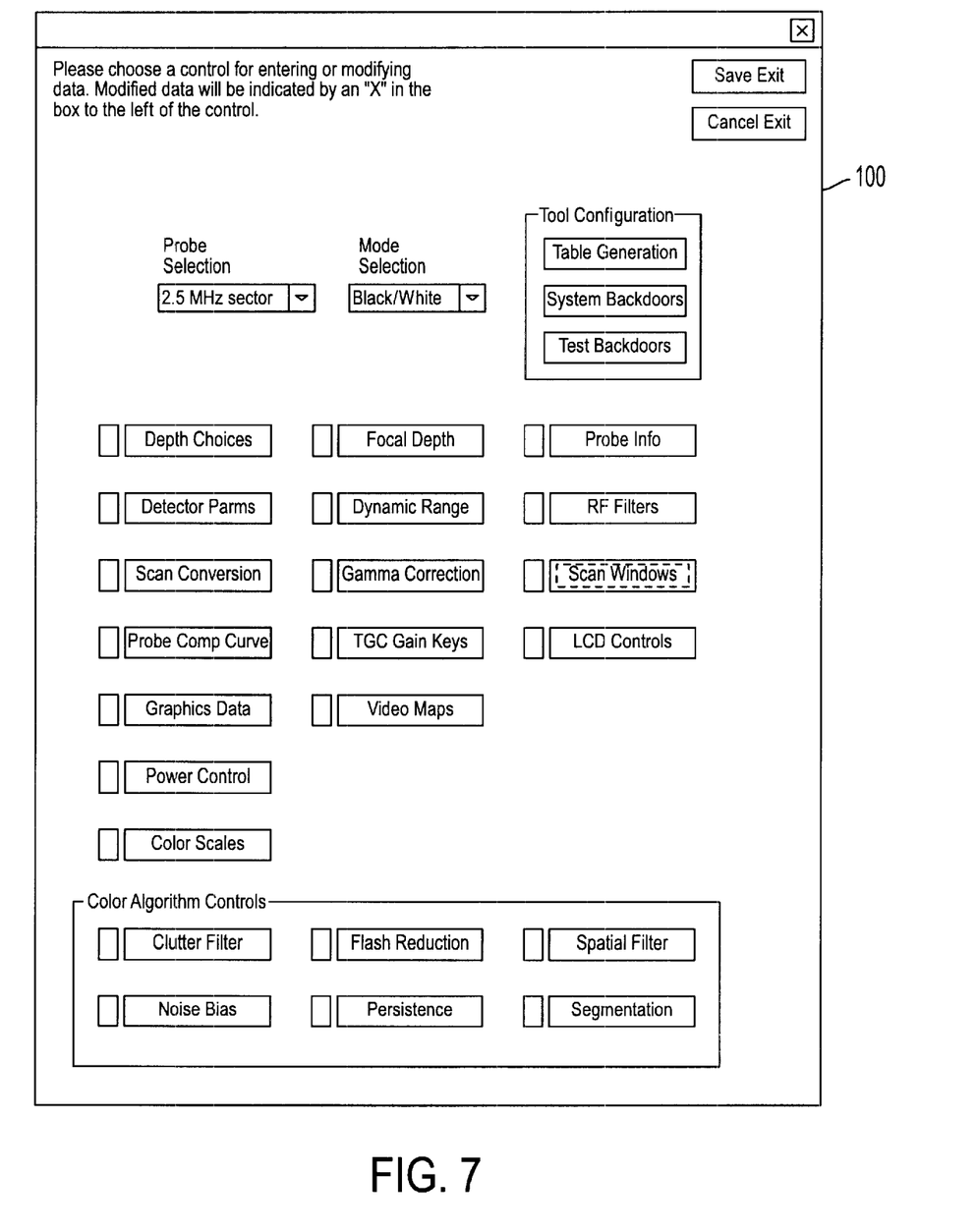
FIGS. 7–9 are diagrams illustrating detailed examples of screen displays, according to an embodiment of the present invention.

FIG. 7 is a diagram illustrating a more detailed example of a main screen display 100 which might be provided by software program 20, according to an embodiment of the present invention. Thus, main screen display 100 is a more detailed example corresponding to main screen display 39 in FIG. 3, and would represent a virtual control panel provided by software program 20. Main screen display 100 shows examples many different types of user controls which might be provided.

Figure 8:
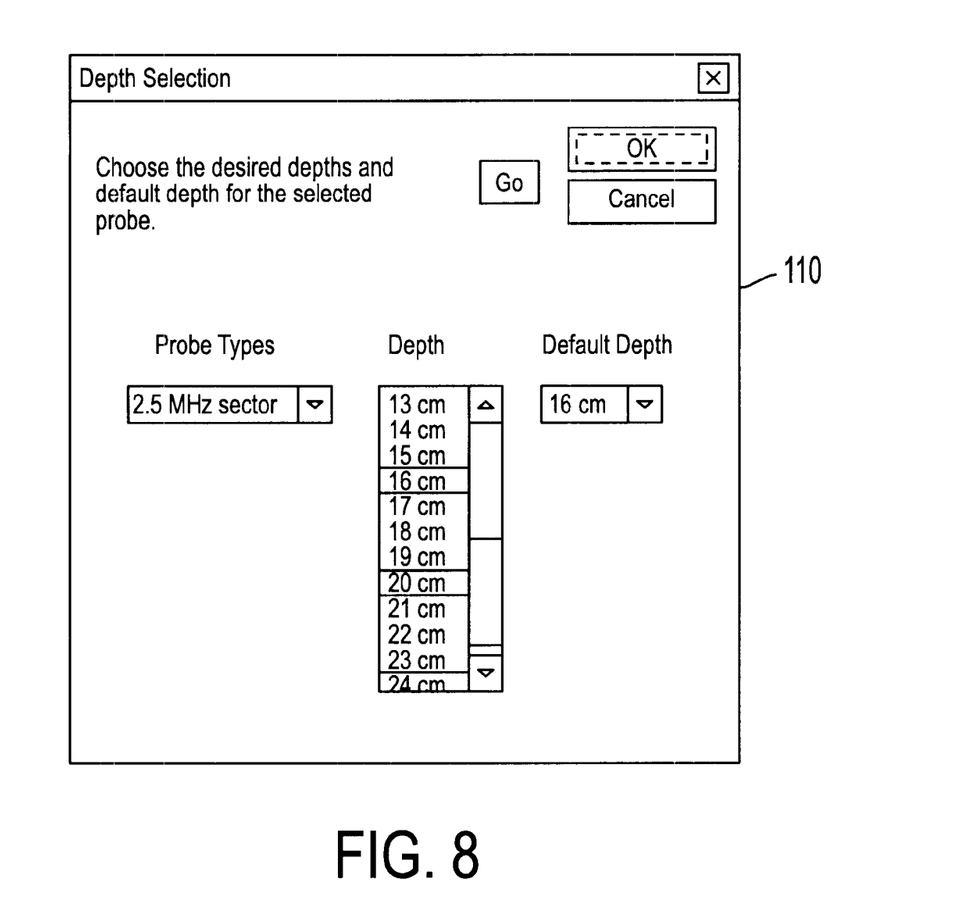

FIG. 8 is a diagram illustrating a more detailed example of a screen display 110 which might be provided by software program 20 after "DEPTH CHOICES" is selected in main screen display 100 of FIG. 7, according to an embodiment of the present invention. Thus, screen display 110 is a more detailed example corresponding to screen display 42 in FIG. 4.

Figure 9:
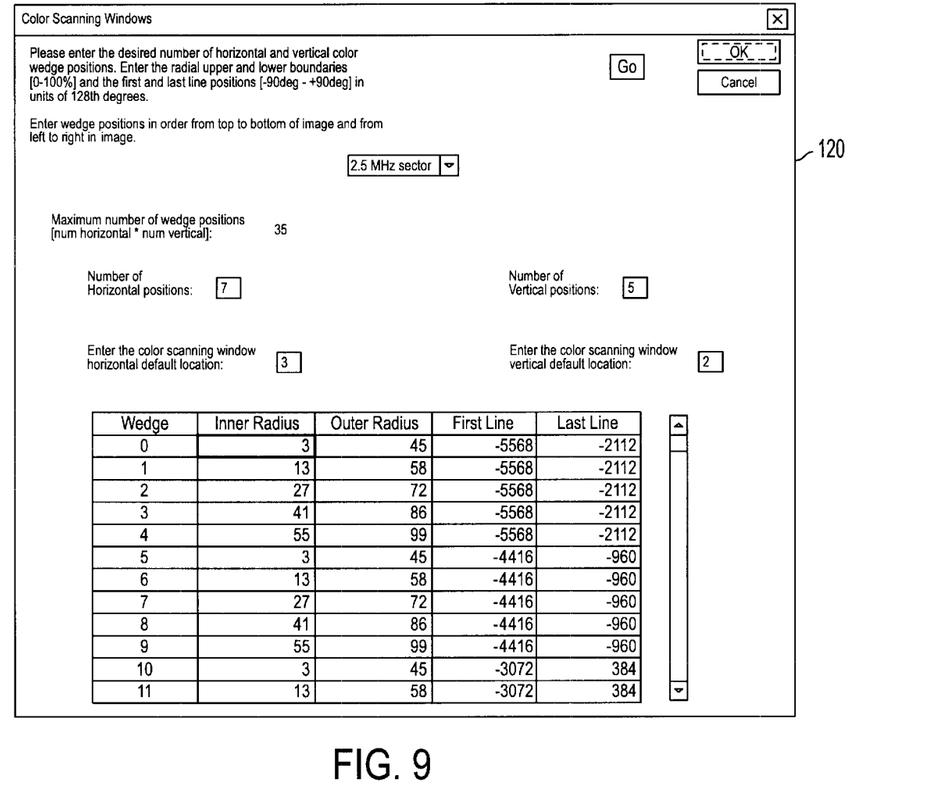

FIG. 9 is a diagram illustrating a detailed example of a screen display 120 which might be provided by software program 20 after "SCAN WINDOWS" is selected in main screen 100 of FIG. 7, according to an embodiment of the present invention.

In various of the above embodiments of the present invention, computer 22 is shown as being directly connected to ultrasonic imaging device 24, and parameters being stored in memory 26 inside ultrasound imaging device 24. However, the present invention is not limited to a direct connection between computer 22 and ultrasonic imaging device 24, and the parameters being stored inside ultrasound imaging device 24.

Figure 10:
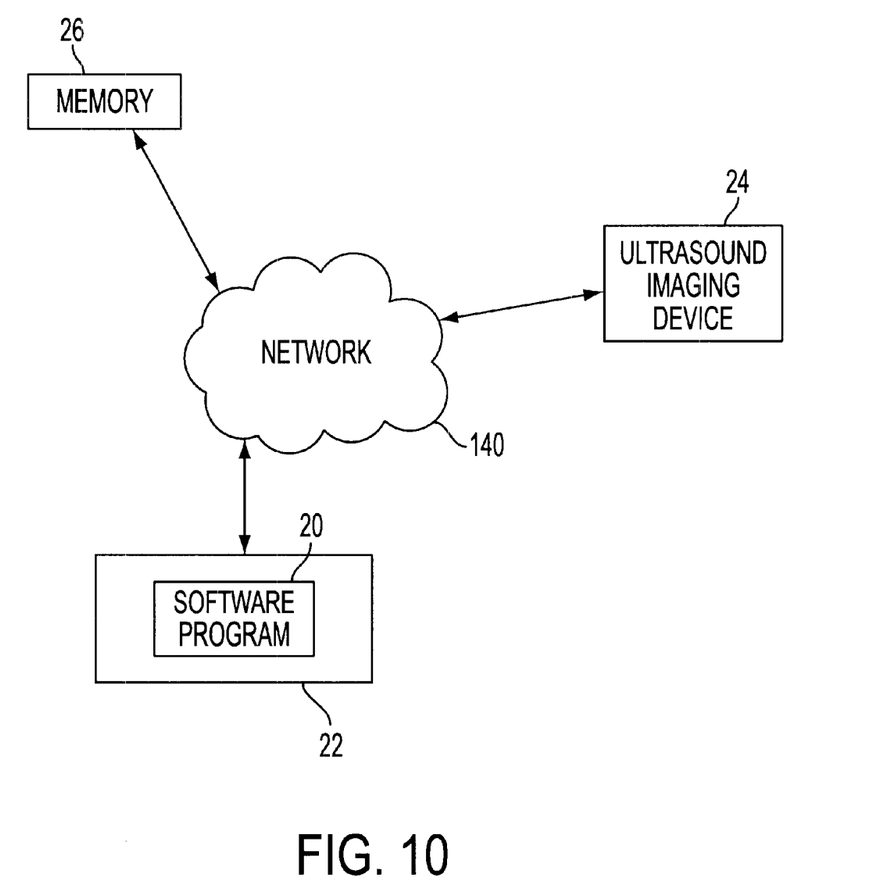
FIG. 10 is a diagram illustrating a computer connected to an ultrasound imaging device through a network, according to an embodiment of the present invention.

For example, FIG. 10 is a diagram illustrating computer 22 connected to ultrasound imaging device 24 through a network 140, according to an embodiment of the present invention. Network 140 might be an optical communications network, an electrical communications network, a wireless communications network, a local area network (LAN), a wide area network (WAN), or any combination of these. For example, network 140 might be the Internet.

Further, in some embodiments of the present invention, the calculated parameters might not be stored inside ultrasound imaging device 24. For example, as shown in FIG. 10, parameters are stored in memory 26 connected to ultrasound imaging device 24 through network 140. Moreover, different networks can be used to connect computer 22 to ultrasound imaging device 24, to connect computer 22 to memory 26, and to connect memory 26 to ultrasound imaging device 24. Preferable, parameters are stored in a location that is quickly accessed by ultrasound imaging device 24 during runtime when ultrasonic images are generated, to avoid runtime delays.

The present invention relates to the use of virtual control panels, such as those provided by software 20, or that might be provided on ultrasound imaging device 24 to display user controls 29. The use of virtual control panels, with virtual buttons or other virtual selection mechanisms that can be changed via software, is well-known.

The above embodiments of the present invention relate to parameters being stored in a "table." However, the present invention is not limited to any specific type of data structure for storing parameters. Instead, other types of appropriate data structures can be used to store parameters.

Although a few preferred embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus comprising:

a processor;

a memory operatively coupled to the processor, the memory comprising a software program executing externally to an ultrasound imaging device, the software program entering a user control value for the ultrasound imaging device and calculating a parameter based on the entered user control value, the parameter being transferred to the ultrasound imaging device and then controlling a parametrically defined machine in the ultrasound imaging device to generate ultrasound images.

2. An apparatus as in claim 1, wherein the ultrasound imaging device is a portable ultrasound imaging device weighing less than fifteen pounds.

3. An apparatus as in claim 1, wherein the ultrasound imaging device is a portable ultrasound imaging device; and the software program executes on a portable computer which is an independent device from the portable ultrasound imaging device.

4. An apparatus as in claim 1, wherein the transferred parameter is stored in a table in the ultrasound imaging device.

5. An apparatus comprising:

a processor; and a memory operatively coupled to the processor, the memory comprising a software program executing externally to an ultrasound imaging device, the software program entering a user control values for the ultrasound imaging device and calculating parameters based on the entered user control values, the parameters being transferred to the ultrasound imaging device and then controlling parametrically defined machines in the ultrasound imaging device to generate ultrasound images.

6. An apparatus as in claim 5, wherein the software program is executed on a portable computer external to the ultrasound imaging device.

7. An apparatus as in claim 5, wherein the ultrasound imaging device is a portable ultrasound imaging device weighing less than fifteen pounds.

8. An apparatus as in claim 5, wherein the ultrasound imaging device is a portable ultrasound imaging device; and the software program is executed on a portable computer which is an independent device from the portable ultrasound imaging device.

9. An apparatus as in claim 5, wherein the software program stores the calculated parameters in tables in the ultrasound imaging device.

10. An apparatus as in claim 5, wherein the entered user control values indicate a subset of a larger universe of user control values for the ultrasound imaging device, the transferred parameters allowing a user of the ultrasound imaging device to select from the subset to control the ultrasound imaging device.

11. An apparatus as in claim 6, wherein the entered user control values indicate a subset of a larger universe of user control values for the ultrasound imaging device, the transferred parameters allowing a user of the ultrasound imaging device to select from the subset to control the ultrasound imaging device.

12. An apparatus as in claim 8, wherein the entered user control values indicate a subset of a larger universe of user control values for the ultrasound imaging device, the transferred parameters allowing a user of the ultrasound imaging device to select from the subset to control the ultrasound imaging device.

13. An apparatus comprising:

an ultrasound imaging device; and a software program executing externally to the ultrasound imaging device, the software program entering user control values for the ultrasound imaging device and calculating parameters based on the entered user control values, the parameters being transferred to the ultrasound imaging device, wherein the ultrasound imaging device includes at least one parametrically defined machine controlled by the transferred parameters to generate ultrasound images.

14. An apparatus as in claim 13, further comprising:

a computer, external to the ultrasound imaging device, on which the software program is executed.

15. An apparatus as in claim 13, wherein the ultrasound imaging device is a portable ultrasound imaging device weighing less than fifteen pounds.

16. An apparatus as in claim 13, wherein the ultrasound imaging device is a portable ultrasound imaging device, the apparatus further comprising:

a computer, external to the ultrasound imaging device, on which the software program is executed.

17. An apparatus as in claim 13, wherein the transferred parameters are stored in tables in the ultrasound imaging device.

18. An apparatus as in claim 13, wherein the entered user control values indicate a subset of a larger universe of user control values for the ultrasound imaging device, the transferred parameters allowing a user of the ultrasound imaging device to select from the subset to control the ultrasound imaging device.

19. An apparatus comprising:

a software program executing externally to an ultrasound imaging device, the software program entering user control values for the ultrasound imaging device and calculating parameters based on the entered user control values, the parameters being stored in a location accessible by the ultrasound imaging device, the stored parameters controlling at least one parametrically defined machine in the ultrasound imaging device to generate ultrasonic images.

20. An apparatus comprising:

a software program executing externally to an ultrasound imaging device, the software program including means for entering user control values for the ultrasound imaging device and for calculating parameters based on the entered user control value; and means for storing the calculated parameters so that the stored parameters are accessible by the ultrasound imaging device to control parametrically defined machines in the ultrasound imaging device to generate ultrasound images.

21. An apparatus comprising:

an imaging device;

an input means external to the imaging device for entering user control values for the imaging device;

a memory means for storing the user control values; and an external processor operatively coupled to the imaging device, the input means, and the memory, the processor capable of calculating parameters based on the entered user control values, the parameters being transferred to the imaging device to generate images.

* * * * *